(12) United States Patent
Smith et al.

(10) Patent No.: US 7,645,866 B2
(45) Date of Patent: Jan. 12, 2010

(54) METHODS OF PRODUCING AND SEQUENCING MODIFIED POLYNUCLEOTIDES

(75) Inventors: Douglas R. Smith, Gloucester, MA (US); Kevin J. McKernan, Marblehead, MA (US)

(73) Assignee: Life Technologies Corporation, Carlsbad, CA (US)

( * ) Notice: Subject to any disclaimer, the term of this patent is extended or adjusted under 35 U.S.C. 154(b) by 425 days.

(21) Appl. No.: 11/476,423

(22) Filed: Jun. 28, 2006

(65) Prior Publication Data

US 2007/0026438 A1 Feb. 1, 2007

Related U.S. Application Data

(60) Provisional application No. 60/694,783, filed on Jun. 28, 2005.

(51) Int. Cl.
C07H 21/04 (2006.01)
C12Q 1/68 (2006.01)
C12P 19/34 (2006.01)
B01L 3/00 (2006.01)

(52) U.S. Cl. .................. 536/23.1; 536/24.3; 536/24.33; 435/6; 435/91.1; 435/91.2; 422/61

(58) Field of Classification Search ............ 435/6, 435/91.1, 91.2; 536/23.1, 24.3, 24.33; 422/61
See application file for complete search history.

(56) References Cited

U.S. PATENT DOCUMENTS 6,087,095 A 7/2000 Rosenthal et al.
6,117,634 A 9/2000 Langmore et al.
6,500,650 B1 12/2002 Stanton, Jr. et al.
6,537,757 B1 3/2003 Langmore et al.

FOREIGN PATENT DOCUMENTS

| WO | WO 93/21340 | 10/1993 |
|---|---|---|
| WO | WO 98/14610 A2 | 4/1998 |
| WO | WO 98/39485 | 9/1998 |
| WO | WO 00/18967 | 4/2000 |
| WO | WO 03/076037 A2 | 9/2003 |
| WO | WO 2007/002890 A2 | 1/2007 |

OTHER PUBLICATIONS

Mag, M., et al., "Synthesis and Selective Cleavage of an Oligodeoxynucleotide Containing a Bridged Internucleotide 5'-Phosphorothioate Linkage," *Nucleic Acids Research*, 19(7):1437-1441 (1991).
Vyle, J.S., et al., "Sequence-and Strand-Specific Cleavage in Oligodeoxyribonucleotides and DNA Containing 3'-Thiothymidine," *Biochemistry*, 31(11):3012-3018 (1992).
Sauer, S., et al., "A Novel Procedure for Efficient Genotyping of Single Nucleotide Polymorphisms," *Nucleic Acids Research*, 28(5):E13, (2000).

*Primary Examiner*—Jezia Riley

(57) ABSTRACT

The present invention encompasses methods for producing a modified polynucleotide sequence that comprises a (e.g., one or more) phosphorothiolate linkage, methods for determining a polynucleotide sequence comprising a (e.g., one or more) phosphorothiolate linkage, and methods for separating forward and reverse extension products that comprise a (e.g., one or more) phosphorothiolate linkage. The invention also encompasses kits for producing and/or determining the sequence of a modified polynucleotide that comprises a (e.g., one or more) phosphorothiolate linkage.

19 Claims, 5 Drawing Sheets

(SEQ ID NO:3)

(SEQ ID NO:4)

(SEQ ID NO:5)
(SEQ ID NO:6)

(SEQ ID NO: 7)

(SEQ ID NO: 8)

METHODS OF PRODUCING AND SEQUENCING MODIFIED POLYNUCLEOTIDES

RELATED APPLICATIONS

This application claims the benefit of U.S. Provisional Application No. 60/694,783, filed on Jun. 28, 2005. The entire teachings of the above application are incorporated herein by reference.

GOVERNMENT SUPPORT

The invention was supported, in whole or in part, by a grant HG00357 from the National Institutes of Health. The Government has certain rights in the invention.

BACKGROUND OF THE INVENTION

Widespread efforts have been made in recent years to determine the sequence of the human genome, as well as the genomes of various other organisms. The advent of genomics has relied upon accurate and efficient DNA sequencing techniques, and the ability to determine the nucleotide sequence of a gene remains an essential component of molecular genetic research. The widespread use of DNA sequencing in biological research necessitates the development of new DNA sequencing techniques that are simpler and more efficient than traditional, commonly-used techniques.

Classical DNA sequencing techniques, such as the Sanger chain termination method (Sanger, F., et al. *Proc. Natl. Acad. Sci. USA* 74: 5463-5467 (1977); incorporated herein by reference) and the Maxam and Gilbert chemical cleavage method (Maxam, A. M. and Gilbert, W. *Proc. Natl. Acad. Sci. USA* 74: 560-564 (1977); incorporated herein by reference), are somewhat cumbersome and inefficient, as both of these approaches require researchers to perform multiple reactions in order to derive a nucleotide sequence. Attempts to simplify DNA sequencing by coupling a single DNA amplification/synthesis reaction with sequence analysis (i.e., direct sequencing) have shown limited success, because these techniques often result in DNA damage and/or degradation (Das et al., *Physiol Genomics* 6: 57-80 (2001)), as well as low fidelity DNA synthesis (Lin et al., *Biochemistry* 40: 8749-8755 (2001); Xia et al., *Proc Natl Acad Sci USA* 99: 6597-6602 (2002); U.S. Pat. No. 5,939,292; U.S. Pat. No. 6,329,178; and U.S. Pat. No. 6,887,690).

Presently, there is a clear need to develop improved methods of sequencing DNA. More specifically, there is a need to develop reliable and efficient direct sequencing techniques that yield accurate DNA sequence information.

SUMMARY OF THE INVENTION

The invention of the instant application provides new methods of sequencing nucleic acids (e.g., DNA), as well as improved methods for performing direct nucleic acid (e.g., DNA) sequencing. The present invention is based, in part, on the discovery that nucleic acid polymerases (e.g., DNA polymerases) are capable of incorporating thiol-nucleoside triphosphates (e.g., 5' thiol-nucleoside triphosphates, 3' thiol-nucleoside triphosphates) into a growing polynucleotide strand to generate a polynucleotide sequence that comprises at least one phosphorothiolate linkage.

Accordingly, the invention encompasses a method for producing a modified polynucleotide sequence that comprises a (one or more) phosphorothiolate linkage. The method comprises annealing at least one primer to a template polynucleotide sequence and extending the primer in the presence of one or more nucleoside triphosphates, wherein at least one of the nucleoside triphosphates is modified, such that a polynucleotide sequence that comprises a phosphorothiolate linkage is produced.

In a particular embodiment, the invention provides a method for producing a modified polynucleotide sequence that comprises a 3' phosphorothiolate linkage. The method comprises annealing at least one primer to a template polynucleotide sequence and extending said primer in the presence of one or more nucleoside triphosphates, wherein at least one of the nucleoside triphosphates in the mixture is a modified nucleoside triphosphate comprising the general structure [I]:

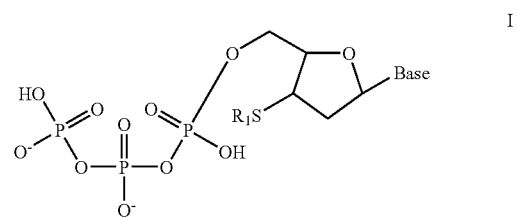

such that a polynucleotide sequence comprising at least one modified nucleotide is produced. The modified polynucleotide sequence comprises a 3' phosphorothiolate linkage, illustrated by the general structure [II]:

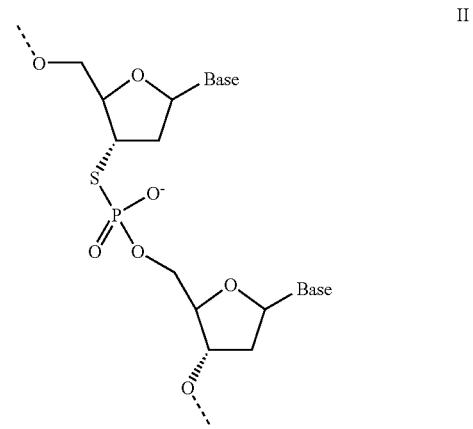

$R_1$ in general structure [I] can be, for example, hydrogen (—H), a substituted or non-substituted: alkyl, akenyl, alkynyl, or aryl group, or $R_2$, wherein $R_2$ can be, for example, —SH, or —$SR_3$, and wherein $R_3$ can be, for example, a substituted or non-substituted: alkyl, akenyl, alkynyl, or aryl group. In a particular embodiment, $R_1$ is —$SCH_3$.

In another embodiment, the invention provides a method for producing a modified polynucleotide sequence that comprises a 5' phosphorothiolate linkage. The method comprises annealing at least one primer to a template polynucleotide sequence and extending said primer in the presence of one or more nucleoside triphosphates, wherein at least one of the nucleoside triphosphates is a modified nucleoside triphosphate comprising the general structure [III]:

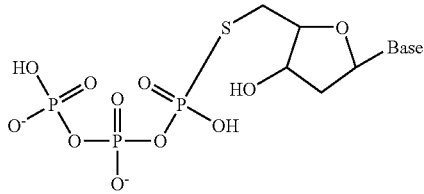

III such that a modified polynucleotide sequence is produced. The modified polynucleotide sequence comprises a 5' phosphorothiolate linkage, illustrated by the general structure [IV]:

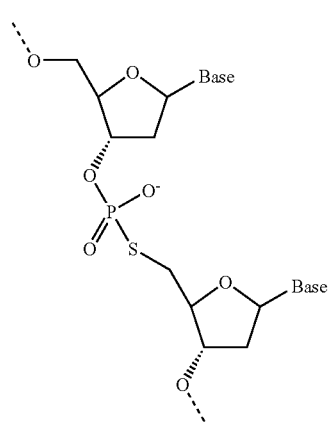

IV

The present invention also encompasses a method for determining (e.g., sequencing) a polynucleotide sequence comprising annealing a plurality of primers to a plurality of template polynucleotide sequences and extending the plurality primers in the presence of nucleoside triphosphates, wherein at least one of the nucleoside triphosphates is modified, thereby producing a plurality of extension products that comprise a modified nucleotide sequence having one or more phosphorothiolate linkages. The phosphorothiolate linkages in the extension products are cleaved under conditions in which a plurality of fragments are produced. The fragments that comprise the primer are identified, and the nucleotide at the 3' end of each fragment that comprises the primer is identified, such that the polynucleotide sequence can be determined.

For example, the fragments that comprise the primer can be identified (e.g., using a tag on the primer) and resolved (e.g., on a solid support, such as a gel), and the sequence of the polynucleotide can be determined (e.g., by detecting the length of the fragment for which the nucleotide at its 3' end is known; by detecting a tag present on the nucleotide at the 3' end, thereby identifying the nucleotide at the 3' end), as will be understood by one of skill in the art. The fragments attached to a primer can be identified either directly or indirectly, using one or more of a variety of previously-described techniques in the art, such as, for example, by using an isolating means that binds to and/or recognizes a tag on each primer. In the methods for determining a polynucleotide sequence, the phosphorothiolate linkage can be cleaved using, for example, $Ag^+$, $Hg^{++}$ and/or $Cu^{++}$. In particular embodiments, the methods comprise cleaving the phosphorothiolate linkage using $Ag^+$ ions at a pH of about 7.0 and at a temperature of about 22° C. to about 37° C.

In a particular embodiment, the one or more modified nucleoside triphosphates comprises a general structure [I]:

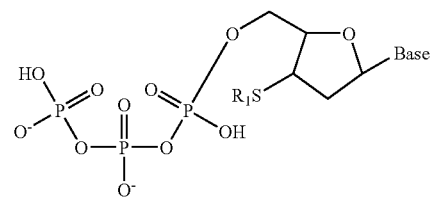

I such that the modified nucleotide sequences that are produced comprise a general structure [II]:

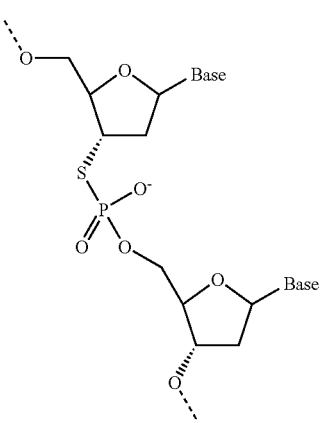

II wherein the general structure [II] comprises at least one 3' phosphorothiolate linkage.

$R_1$ in general structure [I] can be, for example, hydrogen (—H), a substituted or non-substituted: alkyl, akenyl, alkynyl or aryl group, or $R_2$, wherein $R_2$ can be, for example, —SH, or —$SR_3$, and wherein $R_3$ can be, for example, a substituted or non-substituted: alkyl, akenyl, alkynyl, or aryl group. In a particular embodiment, $R_1$ is —$SCH_3$.

In another embodiment, the one or more nucleoside triphosphates comprise the general structure [III]:

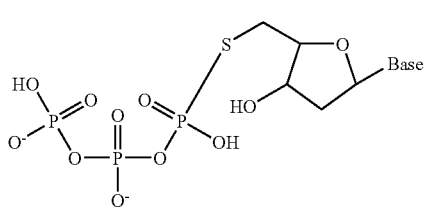

III such that the modified nucleotide sequences that are produced comprise a general structure [IV]:

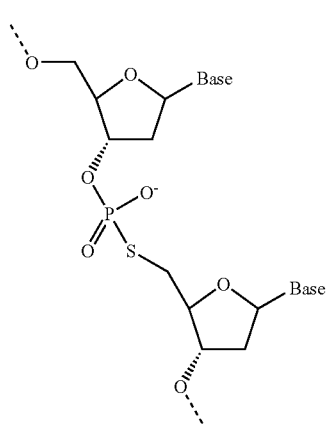

wherein the general structure [IV] comprises at least one 5' phosphorothiolate linkage.

In a further embodiment, the methods for determining a polynucleotide sequence also comprise isolating the cleaved fragments that comprise a primer, prior to identifying the length of the polynucleotide, thereby identifying the nucleotide at the 3' end of the fragments by virtue of the modified nucleotide used in the extension reaction, or identifying the nucleotide at the 3' end of the fragments by detecting a tag on the nucleotide. In a particular embodiment, the fragments that comprise a primer are isolated using an isolating means that specifically recognizes a tag on the fragments (e.g., by binding of the isolating means to a tag on each primer). As used herein, the term "isolated fragment" refers to a preparation of fragments that is purified from, or otherwise substantially free of, other components from the extension and/or cleavage reactions, including, but not limited to, cleavage fragments that are not attached to a primer, buffers, salts, metal ions, unincorporated nucleotides, nucleic acid templates and enzymes. The term "isolating means", as used herein, refers to a means, such as a solid support, which comprises a moiety that specifically recognizes, and binds to, a partner moiety on a substance to be isolated.

The invention is also directed to methods for separating one or more forward extension products from one or more reverse extension products, comprising annealing a plurality of first primers and a plurality of second primers to a plurality of template polynucleotide sequences that comprise a sense nucleotide strand and an antisense nucleotide strand, wherein the first primer anneals to the sense strand and the second primer anneals to the antisense strand and wherein at least one primer (e.g., the first primer, the second primer) comprises a tag. The first and second primers are extended in the presence of one or more nucleoside triphosphates wherein at least one of the nucleoside triphosphates is modified, thereby producing a plurality of extension products that comprise a modified nucleotide sequence having one or more phosphorothiolate linkages. In particular, as will be understood by a person of skill in the art, extension of a first primer annealed to a sense nucleotide strand produces a reverse extension product and extension of a second primer annealed to an antisense nucleotide strand produces a forward extension product. The phosphorothiolate linkages in the modified nucleotide sequences are cleaved under conditions in which a plurality of fragments of the reverse extension product and a plurality of fragments of the forward extension product are produced. The fragments of the reverse extension product that comprise the first primer are then separated from the fragments of the forward extension product that comprise the second primer (e.g., using a tag on the first and/or second primer), thereby separating forward and reverse extension products. For example, one or more reverse extension products that comprise a first primer, which comprises a biotin tag, are separated from fragments of the forward extension product that comprise the second primer, which do not comprise a biotin tag by binding to, for example, streptavidin.

In a particular embodiment, the first primer and the second primer each comprise a tag, wherein the tag on the first primer is distinct from the tag on the second primer. Accordingly, the fragments of the reverse extension product that comprise the first primer can be separated from the fragments of the forward extension product that comprise the second primer using the distinct tags on the first and second primers.

The instant invention also encompasses kits that comprise one or more nucleoside triphosphates, wherein at least one of the nucleoside triphosphates is a modified thiol-nucleoside triphosphate, and a nucleic acid polymerase.

In a particular embodiment, the at least one modified thiol-nucleoside triphosphate comprises the general structure [I]:

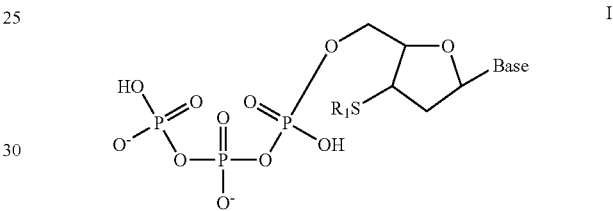

$R_1$ in general structure [I] can be, for example, hydrogen (—H), a substituted or non-substituted: alkyl, akenyl, alkynyl or aryl group, or $R_2$, wherein $R_2$ can be, for example, —SH, or —$SR_3$, and wherein $R_3$ can be, for example, a substituted or non-substituted: alkyl, akenyl, alkynyl or aryl group. In a particular embodiment, $R_1$ is —$SCH_3$.

In another embodiment, the at least one modified thiol-nucleoside triphosphate comprises the general structure [III]:

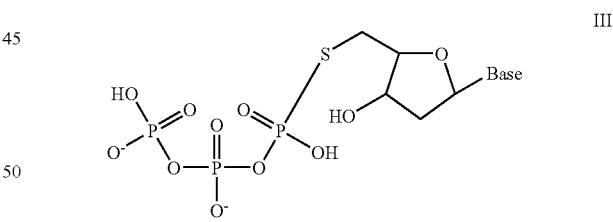

BRIEF DESCRIPTION OF THE DRAWINGS

FIG. 1A is a schematic depicting primer extension of a DNA template using a mixture of unmodified nucleoside triphosphates (pppN, also referred to herein as dNTP) and modified 3'-thiol-nucleoside triphosphates (pppAs, pppTs, pppGs, and pppCs, also referred to herein as pppA-s, pppT-s, pppG-s, pppC-s, sdATP, sdTTP, sdGTP, sdCTP, dAsTP, dTsTP, dGsTP, dCsTP, As, Ts, Gs and Cs). Each of the four 3'-thiol-nucleoside triphosphates is labeled with a distinct fluorophore, indicated by a colored star. The DNA primer (red) is attached to an affinity probe or tag, shown as a gray pentagonal structure at the 5' end of the primer.

FIG. 1B is a schematic depicting a DNA strand (top) which has incorporated multiple labeled 3'-thiol nucleotides (As, Ts, Gs, Cs) following primer extension by DNA polymerase on a DNA template (bottom strand).

FIG. 1C is a schematic depicting the selective cleavage of DNA strands containing 3'-thiol nucleotides in the presence of $AgNO_3$. Cleavage occurs at the 3' end of each modified 3'-thiol nucleotide and results in the generation of several labeled cleavage products.

FIG. 1D is a schematic depicting the purification of several different 5' extension products following $AgNO_3$-induced cleavage of DNA strands containing 3'-thiol nucleotides. DNA cleavage products are isolated using a solid support (red circle), which contains a molecule (blue cross) that binds to the affinity tag on the primer (gray pentagon). Therefore, only the 5'-most DNA fragments, which comprise the primer sequence, are recovered. All other labeled fragments are washed away.

FIG. 2A is a schematic depicting bidirectional PCR amplification of DNA using a mixture of unmodified nucleoside triphosphates (pppN) and modified 3'-thiol-nucleoside triphosphates (pppA-s, pppT-s, pppG-s, and pppC-s). The four 3'-thiol-nucleoside triphosphates are differentially labeled with distinct fluorophores, indicated by stars of different colors. The forward DNA primer (red) and reverse DNA primer (green) are attached to different affinity probes, shown as a gray pentagon (forward primer) or purple hexagon (reverse primer). The DNA duplex at the bottom of the Figure has incorporated multiple labeled 3'-thiol nucleotides (As, Ts, Gs, Cs) following primer extension by DNA polymerase.

FIG. 2B is a schematic depicting the selective cleavage of DNA strands containing 3'-thiol nucleotides in the presence of $AgNO_3$. Cleavage occurs at the 3' end of each modified 3'-thiol nucleotide and results in the generation of several labeled cleavage products.

FIG. 2C is a schematic depicting the purification of 5' extension products following $AgNO_3$-induced cleavage of forward- and reverse-primed DNA strands containing 3'-thiol nucleotides. DNA cleavage products generated from the forward-primed strand are isolated using a solid support (red circle), which contains a molecule (blue cross) that binds to the affinity tag on the primer (gray pentagon). DNA cleavage products generated from the reverse-primed strand are isolated using a solid support (red circle), which contains a molecule (blue sun) that binds to the affinity tag on the reverse primer (purple hexagon). Therefore, the 5'-most DNA fragments from both the forward and reverse strands can be recovered separately and analyzed to determine sequence.

FIG. 3A depicts the chemical structure of 3'-deoxy-dithiomethyl thymidine (dTsTP).

FIG. 3B is a representation showing a dual biotin-labeled DNA template attached to a magnetic bead. The template is hybridized to a primer, which is labeled with Cy5. Five adenine (A) nucleotides are located downstream of the portion of the template sequence that is complementary to the primer sequence.

FIG. 3C depicts the fluorescence profile generated by the Cy5-labeled primer, shown in FIG. 3B. Fluorescence intensity is indicated along the Y-axis, while the size of the labeled product is indicated on the X-axis, where units 0, 1, 2, 3, 4 and 5, indicate that the primer has been extended by 0, 1, 2, 3, 4, or 5 additional nucleotides, respectively. Fluorescence resulting from the label on the primer is indicated by a blue peak. Orange peaks represent the fluorescent profile of size standards.

FIG. 3D depicts the fluorescence profile of the DNA extension products generated when DNA synthesis is conducted in the presence of 3'-deoxy-dithiomethyl thymidine (dTTP) at a 5 μM concentration. Fluorescence intensity is indicated along the Y-axis, while the size of the labeled product is indicated on the X-axis, where units 0, 1, 2, 3, 4 and 5, indicate that the primer has incorporated 0, 1, 2, 3, 4, or 5 additional nucleotides, respectively. Fluorescence resulting from the label on the primer is indicated by a blue peak. The products from this reaction contain anywhere from 0 to 5 modified thymidine residues, with the majority of products containing either 0 or 1 modified nucleotides. Orange peaks represent the fluorescent profile of size standards.

FIG. 3E depicts the fluorescence profile of the DNA extension products generated when DNA synthesis is conducted in the presence of 1.0 mM 3'-deoxy-dithiomethyl thymidine (dTsTP). Fluorescence intensity is indicated along the Y-axis, while the size of the labeled product is indicated on the X-axis, where units 0, 1, 2, 3, 4 and 5 indicate that the primer has incorporated 0, 1, 2, 3, 4, or 5 additional nucleotides, respectively. Fluorescence resulting from the label on the primer is indicated by a blue peak. Nearly all of the products from this reaction have incorporated 5 modified thymidine nucleotides. Orange peaks represent the fluorescent profile of size standards.

FIG. 4A depicts the fluorescence profile (blue) of uncleaved primer extension products generated in the presence of 50 μM 3'-deoxy-dithiomethyl thymidine (dTsTP) nucleoside triphosphates.

FIG. 4B depicts the fluorescence profile of cleaved primer extension products (blue peaks), which were generated in the presence of 50 μM 3'-deoxy-dithiomethyl thymidine (dTsTP) nucleoside triphosphates, following treatment with $AgNO_3$. Orange peaks represent the fluorescent profile of size standards.

FIG. 4C depicts the fluorescence profile (blue) of uncleaved primer extension products generated in the presence of 500 μM 3'-deoxy-dithiomethyl thymidine (dTTP) nucleoside triphosphates.

FIG. 4D depicts the fluorescence profile of cleaved primer extension products (blue peaks), which were generated in the presence of 500 μM 3'-deoxy-dithiomethyl thymidine (dTsTP) nucleoside triphosphates, following treatment with $AgNO_3$. Orange peaks represent the fluorescent profile of size standards.

FIG. 4E depicts the fluorescence profile generated by the labeled-primer alone. Fluorescence resulting from the label on the primer is indicated by a blue peak. Orange peaks represent the fluorescent profile of size standards.

DETAILED DESCRIPTION OF THE INVENTION

Figure 1A:
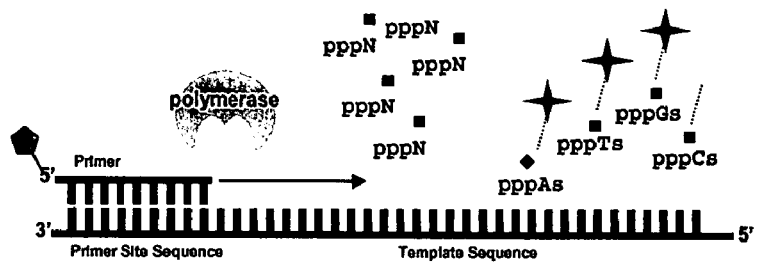
FIG. 1A-FIG. 1D are schematics illustrating the steps involved in producing, cleaving and isolating primer extension products, each of which contains a labeled 3' thiol nucleotide at its 3' end.

The present invention is based, in part, on Applicants' discovery that nucleic acid polymerases can incorporate thiol-nucleoside triphosphates into a growing polynucleotide strand to generate a polynucleotide that comprises one or more phosphorothiolate linkages. Thus, a polynucleotide comprising a phosphorothiolate linkage can be enzymatically synthesized using a polymerase, rather than chemically synthesized. Therefore, the present invention provides a method for producing a modified polynucleotide sequence, wherein the modified polynucleotide sequence comprises a (one or more) scissile internucleoside linkage. As used herein, a "scissile internucleoside linkage" or "scissile linkage" refers to an internucleoside linkage that can be cleaved under conditions that will not substantially cleave phosphodiester bonds. As described herein, nucleic acid polymerases can be used to generate a polynucleotide sequence that comprises one or more scissile internucleoside linkage(s). In a particular embodiment, the scissile internucleoside linkage is a (one or more) phosphorothiolate linkage.

Accordingly, the present invention provides methods for producing a modified polynucleotide sequence. As used herein, the term "modified polynucleotide sequence" refers to a polynucleotide sequence that comprises one or more phosphorothiolate linkages. The method comprises annealing at least one primer to a template polynucleotide sequence and extending the primer in the presence of one or more nucleoside triphosphates, wherein at least one nucleoside triphosphate is modified. As used herein, the phrase "modified nucleoside triphosphate" or "nucleoside triphosphate that is modified" refers to a thiol-nucleoside triphosphate that can be incorporated into a nascent polynucleotide by a nucleic acid polymerase, thereby producing a modified polynucleotide sequence that comprises one or more phosphorothiolate linkages. The term "phosphorothiolate linkage", as used herein, refers to a covalent bond between a sulfur and a phosphorus atom. As used herein, the phrase "polynucleotide sequence comprising a phosphorothiolate linkage" refers to a polynucleotide sequence that comprises a sulfur-phosphorus covalent bond. In particular, a phosphorothiolate linkage results when a sulfur atom replaces one of the bridging oxygen atoms in a phosphodiester bond.

In a particular embodiment, the polynucleotide sequence comprises a 3' phosphorothiolate linkage and is represented by the general structure [II]:

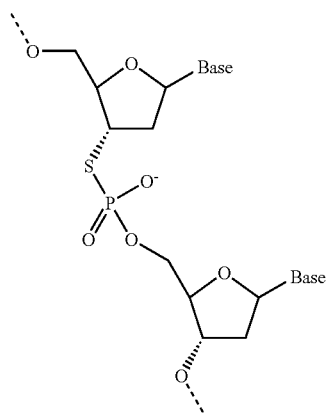

II

A modified polynucleotide sequence comprising a 3' phosphorothiolate linkage can be generated by incorporating one or more 3' thiol-nucleoside triphosphates into a growing polynucleotide strand. As used herein, a "3' thiol-nucleoside triphosphate" refers to a molecule having the general structure [I]:

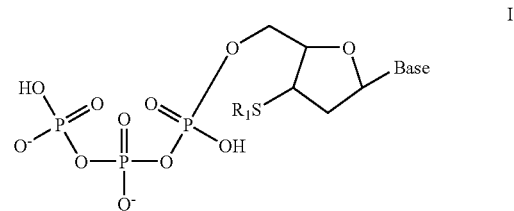

I wherein $R_1$ is hydrogen, a substituted or non-substituted: alkyl, akenyl, alkynyl or aryl group, or $R_2$;

wherein $R_2$ is —SH, or —$SR_3$; and wherein $R_3$ is a substituted or non-substituted: alkyl, akenyl, alkynyl or aryl group.

As used herein, "alkyl", "alkenyl" and "alkynyl" means a group that is saturated or unsaturated, straight-chain, branched, or cyclic, and is derived from a hydrocarbon radical derived by the removal of one hydrogen atom from a single carbon atom of a parent alkane, alkene, or alkyne, respectively. Typical alkyl (e.g., alkyl, cycloalkyl, heteroalkyl), alkenyl (e.g., alkenyl, cycloalkenyl, heteroalkenyl) and alkynyl (e.g., alkynyl, cycloalkynyl, heteroalkynyl) groups, consist of 1 to 12 saturated and/or unsaturated carbons, including, but are not limited to, methyl, ethyl, propyl, butyl, and the like.

As used herein, "aryl" means a monovalent aromatic hydrocarbon radical of 6 to 20 carbon atoms derived by the removal of one hydrogen atom from a single carbon atom of a parent aromatic ring system. Typical aryl groups, which include, for example, cycloaryl and heteroaryl groups, can be substituted or non-substituted and include, but are not limited to, radicals derived from benzene, substituted benzene, naphthalene, anthracene, biphenyl, and the like.

In another embodiment, the polynucleotide sequence comprises a 5' phosphorothiolate linkage and is represented by the general structure [IV]:

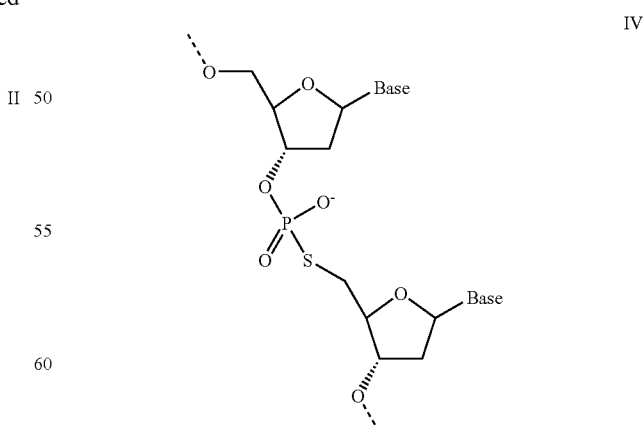

IV

A modified polynucleotide sequence comprising a 5' phosphorothiolate linkage can be generated by incorporating one or more 5' thiol-nucleoside triphosphates into a growing polynucleotide strand. As used herein, a "5' thiol-nucleoside triphosphate" refers to a molecule having the general structure [III]:

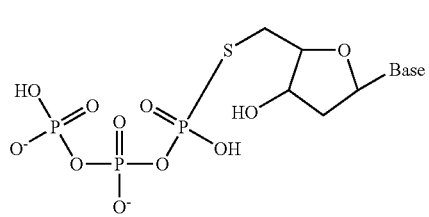

A "nucleoside" comprises a nitrogenous base linked to a sugar molecule. As used herein, the term includes natural nucleosides in their 2'-deoxy and 2'-hydroxyl forms as described in Kornberg and Baker, DNA Replication, 2nd Ed. (Freeman, San Francisco, 1992) and nucleoside analogs. For example, natural nucleosides include adenosine, thymidine, guanosine, cytidine, uridine, inosine, deoxyadenosine, deoxythymidine, deoxyguanosine, and deoxycytidine. Nucleoside "analogs" refers to synthetic nucleosides having modified base moieties and/or modified sugar moieties, e.g., as described generally by Scheit, Nucleotide Analogs (John Wiley, New York, 1980). Such analogs include synthetic nucleosides designed to enhance binding properties, reduce degeneracy, increase specificity, and the like. Nucleoside analogs include 2-aminoadenosine, 2-thiothymidine, pyrrolopyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, 2-thiocytidine, etc. Nucleoside analogs may comprise any of the universal bases mentioned herein.

As used herein, the term "base" refers to the heterocyclic nitrogenous base of a nucleotide or nucleotide analog (e.g., a purine, a pyrimidine, a 7-deazapurine). Suitable bases for use in the methods of the invention include, but are not limited to, adenine, cytosine, guanine, thymine, uracil, hypoxanthine and 7-deaza-guanine. These and other suitable bases will permit a nucleotide bearing the base to be enzymatically-incorporated into a polynucleotide chain or sequence. The base will also be capable of forming a base pair involving hydrogen bonding with a base on another nucleotide or nucleotide analog. The base pair can be either a conventional (standard) Watson-Crick base pair or a non-conventional (non-standard) non-Watson-Crick base pair, for example, a Hoogstein base pair or bidentate base pair.

As used herein, "Watson-Crick base pair" refers to a pair of hydrogen-bonded bases on opposite antiparallel strands of a nucleic acid. The rules of base pairing, which were first elaborated by Watson and Crick, are well known to those of skill in the art. For example, these rules require that adenine (A) pairs with thymine (T) or uracil (U), and guanine (G) pairs with cytosine (C), with the complementary strands anti-parallel to one another. As used herein, the term "Watson-Crick base pair" encompasses not only the standard AT, AU or GC base pairs, but also base pairs formed between non-standard or modified bases of nucleotide analogs capable of hydrogen bonding to a standard base or to another complementary non-standard base. One example of such non-standard Watson-Crick base pairing is the base pairing which involves the nucleotide analog inosine, wherein its hypoxanthine base forms two hydrogen bonds with adenine, cytosine or uracil of other nucleotides.

As used herein, the term "polynucleotide sequence" refers to a nucleic acid molecule (e.g., DNA, RNA) that is produced by the incorporation of two or more nucleoside triphosphates into a single molecule via one or more covalent linkages (e.g., a phosphodiester bond, a phosphorothiolate linkage). A "template polynucleotide sequence" can be any nucleotide sequence for which it is desirable to produce or to obtain sequence information using the methods described herein. The template polynucleotide sequence may be a polynucleotide sequence (e.g., oligonucleotide sequence) and may be single-stranded or double-stranded. A template that is initially provided in double-stranded form can be treated to separate the two strands (e.g., the DNA will be denatured). The template polynucleotide also may be naturally-occurring, isolated or synthetic. Examples of suitable templates include, but are not limited to, genomic DNA, mitochondrial DNA, complementary DNA (cDNA), a PCR product and other amplified nucleotides. RNA may also be used as a template. For example, RNA can be reverse transcribed to yield cDNA, using methods known in the art such as RT-PCR. The template polynucleotide sequence may be used in any convenient form, according to techniques known in the art (e.g., isolated, cloned, amplified), and may be prepared for the sequencing reaction, as desired, according to techniques known in the art. In a particular embodiment, the template polynucleotide sequence comprises DNA. In a further embodiment, the template polynucleotide sequence comprises a sense DNA strand and an antisense DNA strand, wherein at least one primer is annealed to at least one strand (e.g., sense strand, antisense strand) or to both sense and antisense strands.

Template polynucleotides can be obtained from any of a variety of sources. For example, DNA may be isolated from a sample, which may be obtained or derived from a subject. The word "sample" is used in a broad sense to denote any source of a template on which sequence determination is to be performed. The source of a sample may be of any viral, prokaryotic, archaebacterial, or eukaryotic species. The sample may be blood or another bodily fluid containing cells; sperm; and a biopsy (e.g., tissue) sample, among others.

As used herein, the term "primer" refers to an oligonucleotide, which is complementary to the template polynucleotide sequence and is capable of acting as a point for the initiation of synthesis of a primer extension product. In one embodiment, the primer is complementary to the sense strand of a polynucleotide sequence and acts as a point of initiation for synthesis of a forward extension product. In another embodiment, the primer is complementary to the antisense strand of a polynucleotide sequence and acts as a point of initiation for synthesis of a reverse extension product. The primer may occur naturally, as in a purified restriction digest, or be produced synthetically. The appropriate length of a primer depends on the intended use of the primer, but typically ranges from about 5 to about 200; from about 5 to about 100; from about 5 to about 75; from about 5 to about 50; from about 10 to about 35; from about 18 to about 22 nucleotides. A primer need not reflect the exact sequence of the template but must be sufficiently complementary to hybridize with a template for primer elongation to occur, i.e., the primer is sufficiently complementary to the template polynucleotide sequence such that the primer will anneal to the template under conditions that permit primer extension. As used herein, the phrase "conditions that permit primer extension" refers to those conditions, e.g., salt concentration (metallic and non-metallic salts), pH, temperature, and necessary cofactor concentration, among others, under which a given polymerase enzyme catalyzes the extension of an annealed primer. Conditions for the primer extension activity of a wide range of polymerase enzymes are known in the art. As one example, conditions permitting the extension of a nucleic acid primer by Taq polymerase include the following (for any given enzyme, there can and often will be more than one set of such conditions): reactions are conducted in a buffer containing 50 mM KCl, 10 mM Tris (pH 8.3), 4 mM $MgCl_2$, (200 µM of one or more dNTPs and/or a chain terminator may be included, depending upon the type of primer extension or sequencing being performed); reactions are performed at 72° C.

It will be clear to persons skilled in the art that the size of the primer and the stability of hybridization will be dependent to some degree on the ratio of A-T to C-G base pairings, since more hydrogen bonding is available in a C-G pairing. Also, the skilled person will consider the degree of homology between the extension primer to other parts of the amplified sequence and choose the degree of stringency accordingly. Guidance for such routine experimentation can be found in the literature, for example, Molecular Cloning: A Laboratory Manual by Sambrook, J., Fritsch E. F. and Maniatis, T. (1989).

In the methods of the present invention, tags can be used to facilitate the production and/or sequencing of polypeptide sequences. As used herein, a "tag" or "label" are used interchangeably to refer to any moiety that is capable of being specifically detected (e.g., by binding to an isolating means (e.g., a partner moiety)), either directly or indirectly, and therefore, can be used to identify and/or isolate a polynucleotide sequence that comprises the tag. Suitable tags for use in the methods of the present invention can be present on a primer, a modified polynucleotide sequence, a template, or on one or more nucleoside triphosphates (e.g., non-modified or standard nucleoside triphosphates, modified nucleoside triphosphates) and include, among others, affinity tags (e.g., biotin, avidin, streptavidin), haptens, ligands, peptides, nucleic acids, fluorophores, chromophores, and epitope tags that are recognized by an antibody (e.g., digoxigenin (DIG), hemagglutinin (HA), myc, FLAG) (Andrus, A. "Chemical methods for 5' non-isotopic labelling of PCR probes and primers" (1995) in PCR 2: A Practical Approach, Oxford University Press, Oxford, pp. 39-54). Other suitable tags include, but are not limited to, chromophores, fluorophores, haptens, radionuclides (e.g., $^{32}P$, $^{33}P$, $^{35}S$), fluorescence quenchers, enzymes, enzyme substrates, affinity tags (e.g., biotin, avidin, streptavidin, etc.), mass tags, electrophoretic tags and epitope tags that are recognized by an antibody. In certain embodiments, the label is present on the 5 carbon position of a pyrimidine base or on the 3 carbon deaza position of a purine base. In a particular embodiment, the primer comprises at least one tag or label.

In a further embodiment, the primer comprises at least one affinity tag. As defined herein, an "affinity tag" refers to a moiety that can be attached to a nucleoside or nucleoside analog, which can be specifically-bound by a partner moiety. The interaction of the affinity tag and its partner permits the isolation (i.e., specific capture and purification) of molecules bearing the affinity tag. Suitable examples include, but are not limited to, biotin or iminobiotin and avidin or streptavidin. A sub-class of affinity tag is the "epitope tag," which refers to a tag that is recognized and specifically bound by an antibody or an antigen-binding fragment thereof. Examples of epitope tags include the Myc tag, recognized by monoclonal anti-Myc antibodies; FLAG™ tag, recognized by anti-FLAG™ antibodies; and digoxigenin, recognized by anti-digoxigenin antibodies. In one embodiment, the primer comprises a biotin tag. In another embodiment, the primer comprises a digoxigenin tag.

In another embodiment, the primer comprises a tag (e.g., a label) that is a fluorophore. Suitable fluorophores can be provided as fluorescent dyes, including, but not limited to Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), CAL dyes, Carboxyrhodamine 6G, carboxy-X-rhodamine (ROX), Cascade Blue, Cascade Yellow, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, Carboxy-fluorescein (FAM), Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Oyster dyes, Pacific Blue, PyMPO, Pyrene, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, and Texas Red-X. In other embodiments, the label is a mass tag or an electrophoretic tag.

In addition to the various detectable moieties mentioned above, the present invention also comprehends the use of tags or labels, such as spectrally resolvable quantum dots, metal nanoparticles or nanoclusters, etc., which may either be directly attached to an oligonucleotide primer or may be embedded in or associated with a polymeric matrix which is then attached to the primer. As mentioned above, detectable moieties need not themselves be directly detectable. For example, they may act on a substrate which is detected, or they may require modification to become detectable.

As described herein, the primers and nucleotide triphosphates can comprise one or more tags or labels (e.g., a first tag, second tag, third tag, fourth tag, fifth tag, sixth tag, seventh tag, eighth tag). The various tags used in the methods can be the same or different (distinct). In a particular embodiment, when more than one tag is used in the method, the tags (e.g., first, second) are different (distinct), such that the primers or nucleoside triphosphates can be separated from one another using the distinct tag or tags.

As will be appreciated by one of ordinary skill in the art, references to templates, primers, etc., generally mean populations or pools of nucleic acid molecules that are substantially identical within a relevant region rather than single molecules. Thus, for example, a "template" generally means a plurality of substantially identical template molecules.

According to the methods of the invention, primer extension is carried out in the presence of one or more nucleoside triphosphates. In one embodiment, the nucleoside triphosphates are a mixture of standard deoxynucleoside triphosphates (also referred to herein as dNTPs (e.g., dATP, dCTP, dGTP, dTTP, dUTP) and pppNs (e.g., pppA, pppC, pppG, pppT)) and modified thiol-deoxynucleoside triphosphates (e.g., 3' and 5' thiol-nucleoside triphosphates (also referred to herein as sdNTPs (e.g., sdATP, sdCTP, sdGTP, sdTTP, sdUTP) and dNsTPs (e.g., dAsTP, dCsTP, dGsTP, dTsTP, dUsTP))). In a particular embodiment, the mixture of nucleoside triphosphates comprises four standard deoxynucleotide triphosphates and one or more thiol-nucleoside triphosphates. Suitable thiol-nucleoside triphosphates include, but are not limited to, those which comprise a base that is either adenine, cytosine, thymine, guanine or uracil. In particular embodiments of the methods of the invention, each standard dNTP is present at a higher concentration than its corresponding modified dNTP (e.g, dCTP is present in the mixture at a higher concentration than the modified thiol-dCTP in the same mixture) so that the modified dNTP will be incorporated less frequently than the standard dNTP, as will be understood by the person of skill in the art.

The modified thiol-nucleoside triphosphates in the mixture of nucleoside triphosphates can be unlabeled or can comprise one or more labels, as described herein. In a particular embodiment, the mixture of nucleotides comprises four labeled thiol-nucleoside triphosphates (e.g., sdCTP, sdTTP, sdATP, and sdGTP). In a particular embodiment, each of the four thiol-nucleoside triphosphates comprises a distinct label, which is not present on any other nucleotide in the mixture. Thus, in certain embodiments, the label is present on the 5 carbon position of a pyrimidine base or on the 7 carbon deaza position of a purine base. A person of skill in the art will recognize that a polynucleotide sequence can be determined, according to the methods of the present invention, by performing a single reaction that utilizes a mixture of four conventional nucleoside triphosphates and four modified 3' thiol-nucleoside triphosphates, wherein each of the four modified 3' thiol-nucleoside triphosphates comprises a distinct label that is not present on any other nucleotide in the mixture.

Extension of a primer (e.g., DNA synthesis) can be accomplished using a nucleic acid polymerase which is capable of enzymatically-incorporating both standard (dNTPs) and modified thiol deoxynucleotides (sdNTPs) into a growing nucleic acid strand. As used herein, the phrase "nucleic acid polymerase enzyme" refers to an enzyme (e.g., naturally-occurring, recombinant, synthetic) that catalyzes the template-dependent polymerization of nucleoside triphosphates to form primer extension products that are complementary to one of the nucleic acid strands of the template nucleic acid sequence. Numerous nucleic acid polymerases are known in the art and are commercially available. Nucleic acid polymerases that are thermostable, i.e., they retain function after being subjected to temperatures sufficient to denature annealed strands of complementary nucleic acids, are particularly useful for the methods of the present invention.

Suitable polymerases for the methods of the present invention include any polymerase known in the art to be useful for recognizing and incorporating standard deoxynucleotides. Examples of such polymerases are disclosed in Table 1 of U.S. Pat. No. 6,858,393, the contents of which are incorporated herein by reference. Many polymerases are known by those of skill in the art to possess a proof-reading, or exo-nucleolytic activity, which can result in digestion of 3' ends that are available for primer extension. In order to avoid this potential problem, it may be desirable to use polymerase enzyme which lack this activity (e.g., exonuclease-deficient polymerases, referred to herein as exo-polymerases). Such polymerases are well known to those of skill in the art and include, for example, Klenow fragment of *E. Coli* DNA polymerase I, Sequenase, exo-*Thermus aquaticus* (Taq) DNA polymerase and exo-*Bacillus stearothermophilus* (Bst) DNA polymerase. In a particular embodiment, incorporation of modified thiol deoxynucleotides (sdNTPs) into DNA is accomplished using a DNA amplification reaction, such as PCR. Therefore, especially suitable polymerases for the methods of the present invention include those that are stable and function at high temperatures (i.e., thermostable polymerases useful in PCR thermal cycling). Examples of such polymerases include, but are not limited to, *Thermus aquati-* *cus* (Taq) DNA polymerase, TaqFS DNA polymerase, thermosequenase, Therminator DNA polymerase, Tth DNA polymerase, Pfu DNA polymerase and Vent (exo-)DNA polymerase. In another embodiment, incorporation of modified thiol-nucleoside triphosphates into RNA is accomplished using an RNA polymerase. Examples of RNA polymerases include, but are not limited to, *E. coli* RNA polymerase, T7 RNA polymerase and T3 RNA polymerases.

The present invention also encompasses a method for determining all or a portion of a polynucleotide sequence comprising: annealing a plurality of primers to a plurality of template polynucleotide sequences; and extending the plurality of primers in the presence of one or more nucleoside triphosphates wherein at least one of the nucleoside triphosphates is modified, thereby producing a plurality of extension products that comprise a modified nucleotide sequence having one or more phosphorothiolate linkages. The phosphorothiolate linkages in the extension products are cleaved under conditions in which a plurality of fragments are produced; and the fragments of the of the extension products that comprise a primer are then identified (e.g., using tags, labels, solid supports and other means described herein), and the nucleotide at the 3' end of the fragments is subsequently identified, such that the polynucleotide sequence can be determined.

In one embodiment, the at least one modified nucleotide comprises a general structure [I]:

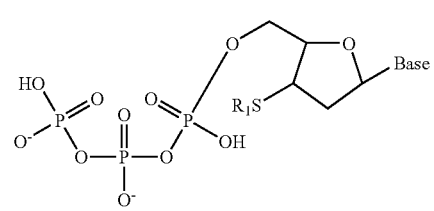

I such that the modified nucleotide sequences that are produced comprise a general structure [II]:

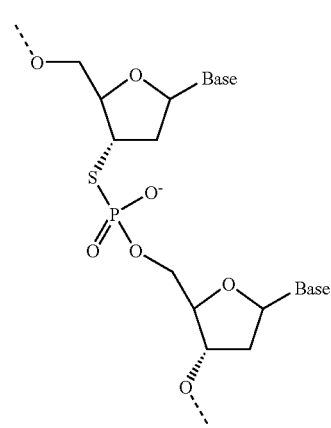

II wherein the general structure [II] comprises at least one 3' phosphorothiolate linkage.

In another embodiment, the at least one modified nucleotide comprises a general structure [III]:

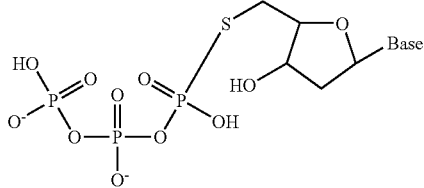

such that the modified nucleotide sequences that are produced comprise a general structure [IV]:

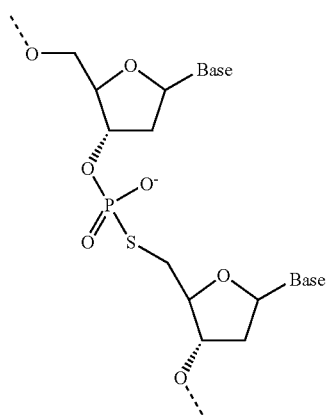

wherein the general structure [IV] comprises at least one 5' phosphorothiolate linkage.

One of skill in the art will recognize that, in order to determine the sequence of a polynucleotide using the methods of the present invention, a ladder of fragments in which each fragment comprises a primer can be produced by cleavage of a plurality of extension products. One of skill in the art will appreciate that four separate extension reactions can be performed in which a different modified dNTP (e.g., thiol-nucleoside triphosphate) is used in each of the four reactions. Upon cleaving the extension products to produce fragments of various sizes and resolving the fragments (e.g., on a gel), four distinct ladders are produced, wherein each fragment in an individual ladder has at its 3' end the same modified nucleotide that was used for the extension reaction. By determining the size of each fragment that has a known nucleotide at its 3' end and comparing the size of the fragments in the four individual ladders, the sequence of the extension product can be determined. Once the sequence of the extension product is known, the sequence of the template polynucleotide, which is the reverse complement of the sequence of the extension product, can be determined.

Alternatively, one of skill in the art will recognize that a single extension reaction comprising 4 modified dNTPs (e.g., thiol-nucleoside triphosphates), wherein each reaction comprises four distinct labels corresponding to the four bases (e.g., a distinct label on more than one modified nucleoside triphosphate, more than one dNTP, more than one primer, more than one etc., and combinations thereof), wherein each distinct label can be used to generate a single sequence ladder representing the different bases. Thus, the ladder comprises fragments that represent the full-length extension product and various 3' truncations thereof. Preferably, all possible 3' truncations of the extension product are produced, such that the complete sequence of the polynucleotide can be determined. By resolving the ladder of fragments (e.g., on a gel), identifying the nucleotide at the 3' end of each fragment (e.g., using the distinct label or tag on the nucleotide, such as a fluorophore) and reading the sequence ladder (e.g., on a gel), beginning with the nucleotide at the 3' end of the smallest fragment and ending with the nucleotide at the 3' end of the largest fragment, the sequence of the polynucleotide can be determined. Once the sequence of the extension product is known, the sequence of the template polynucleotide, which is the reverse complement of the sequence of the extension product, can be determined.

As used herein, the phrase "determining a polynucleotide sequence", "sequencing", and like terms, in reference to polynucleotides, includes determination of partial as well as full sequence information of the polynucleotide. That is, the term includes sequence comparisons, fingerprinting, and like levels of information about a target polynucleotide, as well as the express identification and ordering of each nucleoside of the target polynucleotide within a region of interest. In certain embodiments of the invention "determining a polynucleotide sequence" comprises identifying a single nucleotide, while in other embodiments more than one nucleotide is identified. In certain embodiments of the invention, sequence information that is insufficient by itself to identify any nucleotide in a single cycle is gathered. Identification of nucleosides, nucleotides, and/or bases are considered equivalent herein. It is noted that performing sequence determination on a polynucleotide typically yields equivalent information regarding the sequence of a perfectly complementary (100% complementary) polynucleotide, and thus, is equivalent to sequence determination performed directly on a perfectly complementary polynucleotide. The methods described herein allow partial determination of a sequence, e.g., the identification of individual nucleotides spaced apart from one another in a template. In certain embodiments of the invention, in order to gather more complete information, a plurality of reactions is performed.

In one embodiment of the invention, the identity of one or more nucleotides is determined using the methods described herein, for the purpose of detecting a polymorphism. The term "polymorphism" is given its ordinary meaning in the art and refers to a difference in a nucleotide sequence (e.g., genomic sequence) among individuals (e.g., of the same species). In a particular embodiment, the polymorphism is a "single nucleotide polymorphism" (SNP), which refers to a polymorphism at a single position. In other embodiments of the invention, the methods for determining a polynucleotide sequence are employed to determine the identity of multiple nucleotides (e.g., more than one) in a template polynucleotide sequence.

In particular embodiments, a plurality of extension products that comprises a modified nucleotide sequence having one or more phosphorothiolate linkages are produced using polymerase chain reaction (PCR). Methods for performing PCR are well known in the art and are described, for example, in U.S. Pat. Nos. 4,683,195, 4,683,202, and 4,965,188, and in Dieffenbach, C. and Dveksler, G S, *PCR Primer: A Laboratory Manual*, $2^{nd}$ ed., Cold Spring Harbor Laboratory Press, Cold Spring Harbor, 2003.

The methods for determining a polynucleotide sequence comprise cleaving phosphorothiolate linkages in the extension products under conditions in which a plurality of fragments of the modified nucleotide sequence attached to a plurality of primers are produced. One of skill in the art will recognize that such conditions can also result in the separation of the cleaved fragments from the template polynucleotide sequence to which they are annealed, thereby producing a single-stranded polynucleotide. A phosphorothiolate linkage (3' or 5') in a polynucleotide sequence can be efficiently cleaved according to methods known in the art (Vyle, J. S., et al., Biochemistry 31: 3012-3018 (1992); Sontheimer, E. J., et al., Methods 18: 29-37(1999); Mag, M., et al., Nucleic Acids Res., 19(7):1437-1441 (1991)). For example, cleavage of a phosphorothiolate linkage can be accomplished chemically, by exposing (e.g., contacting) the polynucleotide sequence to certain metal agents. The metal can be, for example, silver (Ag), mercury (Hg), copper (Cu), manganese (Mn), zinc (Zn) or cadmium (Cd), among others. Water-soluble salts that provide $Ag^+$, $Hg^{++}$, $Cu^{++}$, $Mn^{++}$, $Zn^+$ or $Cd^+$ anions (salts that provide ions of other oxidation states can also be used) are particularly useful. Iodide ($I_2$) can also be used. Silver-containing salts such as silver nitrate ($AgNO_3$), or other salts that provide $Ag^+$ ions, are particularly useful in the methods of the present invention.

Suitable conditions for cleaving a phosphorothiolate linkage present in a polynucleotide sequence include, but are not limited to, incubating the polynucleotide sequence with a metal agent, such as $Ag^+$ ions, at a pH in the range of from about 4.0 to about 10.0, from about 5.0 to about 9.0 or from about 6.0 to about 8.0, and at a temperature in the range of from about 15° C. to about 50° C., from about 20° C. to about 45° C., from about 25° C. to about 40° C., from about 22° C. to about 37° C., or from about 24° C. to about 32° C. Particular suitable conditions include, for example, incubation in the presence of 50 mM $AgNO_3$ at about 22 to about 37° C. for at least about 10 minutes at a pH of about 7.0. An example of conditions for a cleavage reaction are described in Example 2. Such conditions can optionally comprise an additional step in which the cleaved fragments are separated from the template polynucleotide sequence to which they are annealed (e.g., incubation at a temperature from about 90° C. to about 100° C. for about 30 seconds to about 60 seconds) prior to or at the same time the phosphorothiolate linkages are cleaved.

In a further embodiment of the invention, the method for determining a polynucleotide sequence additionally comprises isolating a cleaved fragment (e.g., using an isolating means) subsequent to the cleavage reaction. In a particular embodiment, the cleaved fragment that is isolated comprises the primer that was extended in the extension reaction. As used herein, the term "isolated fragment" refers to a preparation of fragments that is purified from, or otherwise substantially free of, other components from the extension and/or cleavage reactions, including, but not limited to, cleavage fragments that are not attached to a primer, buffers, unincorporated nucleotides, nucleic acid templates and enzymes. Such fragments can be isolated using an isolating means, for example, a support (e.g., magnetic beads, agarose or sepharose beads, among others) that comprises a moiety which recognizes and binds to a tag (e.g., a tag on a primer). Examples of pairs of partner moieties that are suitable for the present invention include, but are not limited to, biotin and streptavidin/avidin, or an epitope (e.g., digoxigenin (DIG)) and an antibody that recognizes and binds the epitope (e.g., an anti-DIG antibody).

"Support", as used herein, refers to a matrix on or in which nucleic acid molecules, microparticles, and the like may be immobilized, e.g., to which they may be covalently or noncovalently attached or, in or on which they may be partially or completely embedded so that they are largely or entirely prevented from diffusing freely or moving with respect to one another. The term "microparticle" is used herein to refer to particles having a smallest cross-sectional dimension of 50 microns or less, preferably 10 microns or less. Microparticles may be made of a variety of inorganic or organic materials including, but not limited to, glass (e.g., controlled pore glass), silica, zirconia, cross-linked polystyrene, polyacrylate, poly-methylmethacrylate, titanium dioxide, latex, polystyrene, etc. See, e.g., U.S. Pat. No. 6,406,848, for various suitable materials and other considerations. Magnetically responsive microparticles can be used. The magnetic responsiveness of certain preferred microparticles permits facile collection and concentration of the microparticle-attached templates after amplification, and facilitates additional steps (e.g., washes, reagent removal, etc.). In certain embodiments of the invention a population of microparticles having different shapes (e.g., some spherical and others nonspherical) is employed. In general, any pair of molecules that exhibit affinity for one another such that they form a binding pair may be used to attach microparticles or templates to a substrate. The first member of the binding pair is attached covalently or noncovalently to the substrate, and the second member of the binding pair is attached covalently or noncovalently to the microparticles or templates.

In other embodiments of the invention, the templates are amplified by polymerase chain reaction (PCR) in a semi-solid support, such as a gel having suitable amplification primers immobilized therein. Templates, additional amplification primers, and reagents needed for the PCR reaction are present within the semi-solid support. One or both of a pair of amplification primers is attached to the semi-solid support via a suitable linking moiety, e.g., an acrydite group. Attachment may occur during polymerization. Additional reagents (e.g., templates, second amplification primer, polymerase, nucleotides, cofactors, etc.) may be present prior to formation of the semi-solid support (e.g., in a liquid prior to gel formation), or one or more of the reagents may be diffused into the semi-solid support after its formation. The pore size of the semi-solid support is selected to allow such diffusion. As is well known in the art, in the case of a polyacrylamide gel, pore size is determined mainly by the concentration of acrylamide monomer and to a lesser extent by the crosslinking agent. Similar considerations apply in the case of other semi-solid support materials. Appropriate cross-linkers and concentrations to achieve a desired pore size can be selected.

In certain embodiments of the invention an additive such as a cationic lipid, polyamine, polycation, etc., is included in the solution prior to polymerization, which forms in-gel micelles or aggregates surrounding the microparticles. Methods disclosed in U.S. Pat. Nos. 5,705,628, 5,898,071, and 6,534,262 and U.S. Patent Application Publication No. 2002/0106686, each of which are incorporated herein by reference, may also be used. For example, various "crowding reagents" can be used to crowd DNA near beads for clonal PCR. SPRI® magnetic bead technology and/or conditions can also be employed. See, e.g., U.S. Pat. No. 5,665,572, demonstrating effective PCR amplification in the presence of 10% polyethylene glycol (PEG). In certain embodiments of the inventive methods amplification (e.g., PCR), ligation, or both, are performed in the presence of a reagent such as betaine, polyethylene glycol, PVP-40, or the like. These reagents may be added to a solution, present in an emulsion, and/or diffused into a semi-solid support.

Numerous other supports are known in the art, some of which are described in U.S. Pat. No. 6,828,100, the contents of which are herein incorporated by reference. In general, any of a wide variety of methods known in the art can be used to modify nucleic acids such as oligonucleotide primers, probes, templates, etc., to facilitate the attachment of such nucleic acids to microparticles or to other supports or substrates.

As will be understood by a person of skill in the art, isolated extension products can be identified, either directly or indirectly, using one of many standard and well-known detection methods and/or techniques. Such methods and/or techniques include, but are not limited to, fluorescence detection, spectrophotometric detection, chemical detection and/or electrophoretic detection. In one embodiment, detection of isolated extension products is accomplished by resolving the primer extension products by means of, for example, high-resolution denaturing polyacrylamide/urea gel electrophoresis, capillary separation, or other resolving means; followed by detecting the fragments, for example, using a scanning spectrophotometer or fluorometer. In a particular embodiment, fluorescently-labeled primer extension products are resolved by gel electrophoresis, according to procedures that are well known in the art, and are subsequently detected in the gel using a standard fluorometer.

Electrophoretic separation of the isolated cleavage fragments produces a "ladder" of extension fragments, each fragment starting with the primer and ending with one of the four modified thiol-nucleotides at its 3' end. The sequence of the complement (i.e., the primer extension product), from which the sequence of the template can be deduced, is read directly from the order of fragments on the gel. Techniques for detecting nucleic acid fragments on a gel are well known in the art. Furthermore, one of skill in the art will recognize that the particular method of detection will depend on the specific label comprised by the resolved fragments. For example, if the fragments are labeled with a fluorophore, then standard fluorescence-based techniques can be utilized to detect the fragments in a gel.

The skilled artisan will recognize that a polynucleotide sequence can be determined, according to the methods of the present invention, by performing a single reaction that utilizes a mixture of four conventional nucleoside triphosphates and four modified 3' thiol-nucleoside triphosphates, wherein each of the four modified 3' thiol-nucleoside triphosphates comprises a distinct label that is not present on any other nucleotide in the mixture (e.g., four color sequencing).

Alternatively, one of skill in the art will also recognize that a polynucleotide sequence can be determined, according to the methods of the present invention, by performing four separate reactions to determine the nucleotide sequence of a template when 5' thiol-nucleoside triphosphates are utilized to generate modified polynucleotide sequences comprising one or more 5' phosphorothiolate linkages. In a particular embodiment, each of the four reactions comprises four conventional nucleoside triphosphates and only one of four modified 5' thiol-nucleoside triphosphates, for example, sdCTP, sdATP, sdGTP, or sdTTP. When four reactions are performed using the same template polynucleotide sequence, each with one of the four modified 5' thiol-nucleoside triphosphates, for example, sdCTP, sdATP, sdGTP or sdTTP, the products of the reactions can be cleaved and detected, according to the methods described herein, and analyzed to determine the sequence of the template polynucleotide (see, for example, Sanger, F., et al. *Proc. Natl. Acad. Sci. USA* 74: 5463-5467 (1977) and Maxam, A. M. and Gilbert, W. *Proc. Natl. Acad. Sci. USA* 74: 560-564 (1977), the contents of each are incorporated by reference herein).

In other embodiments of the invention, the methods described herein can be performed using a template polynucleotide sequence comprising a sense and antisense nucleotide strand and two primers, a forward primer and a reverse primer, such that sequence information for both the sense and antisense strands of the template polynucleotide sequence can be determined. In one embodiment, each primer comprises at least one distinct tag that is not present on the other primer. After primer extension is performed to produce extension products that comprise modified polynucleotide sequences having one or more phosphorothiolate linkages, followed by cleavage of the phosphorothiolate linkages in the modified polynucleotide sequences—both performed according to methods described herein—two populations of cleaved extension fragments can be isolated, also according to methods described herein. The first population consists of cleavage fragments, each of which comprises the forward primer, while the second population consists of cleavage fragments, each of which comprises the reverse primer. These populations can be separated from one another and the sequences of the forward and reverse extension products can be determined, as described herein, such that the sequences of both the antisense and sense strands of the template polynucleotide sequence can be determined.

Accordingly, the present invention also provides a method for separating one or more forward extension products from one or more reverse extension products comprising annealing a plurality of first primers and a plurality of second primers to a plurality of template polynucleotide sequences comprising a sense nucleotide strand and an antisense nucleotide strand, wherein the first primer anneals to the sense strand and the second primer anneals to the antisense strand and wherein at least one primer comprises a tag. The first and second primers are extended in the presence of one or more nucleoside triphosphates, wherein at least one of the nucleoside triphosphates is modified, thereby producing a plurality of extension products that comprise a modified nucleotide sequence having one or more phosphorothiolate linkages. The phosphorothiolate linkages in the modified extension products are cleaved under conditions in which a plurality of fragments are produced; and the fragments attached to the first primers are separated from the fragments attached to the second primers.

In a particular embodiment, the first primer and the second primer each comprise a tag, wherein the tag on the first primer is distinct from the tag on the second primer. Accordingly, the fragments of the reverse extension product that comprise the first primer can be separated from the fragments of the forward extension product that comprise the second primer using the distinct tags on the first and second primers. The fragments of the forward and reverse extension products can be identified either simultaneously or in succession.

In another embodiment, two primers, a forward and reverse primer, are used to amplify the template polynucleotide sequence by polymerase chain reaction (PCR), according to procedures that are well known in the art. Forward and reverse primer extension products with at least one phosphorothiolate linkage, whose sequences correspond to the sense and antisense strands of the template sequence, respectively, are generated. These products can then be cleaved, isolated and detected, according to methods described herein, in order to deduce the sequence of the template polynucleotide.

The invention also encompasses a kit, which can comprise one or more modified thiol-nucleoside triphosphates (sdNTPs), conventional nucleoside triphosphates (dNTPs) and/or a nucleic acid polymerase (e.g., Klenow fragment of *E. Coli* DNA polymerase I, Sequenase, exo-*Thermus aquaticus* (Taq) DNA polymerase and exo-*Bacillus stearothermophilus* (Bst) DNA polymerase). The modified sdNTPs can be either labeled or unlabeled. In a particular embodiment, the sdNTPs comprise a fluorescent label (e.g., a fluorophore). In certain embodiments, the detectable label is present on the 5 carbon position of a pyrimidine base or on the 7 carbon deaza position of a purine base. In another embodiment, the standard and modified nucleotides comprise a base, such as, but not limited to, adenine, guanine, cytosine, thymine, uracil, hypoxanthine or 7-deaza-guanine. Such kits can be used, for example, to produce and/or determine the sequence of a modified polynucleotide that comprises a (e.g., one or more) phosphorothiolate linkage.

The modified thiol nucleotides can be either 3' thiol nucleotides or 5' thiol nucleotides. In a particular embodiment the 3' thiol nucleotides comprise either a 3' thiol group (—SH) or a 3' dithiomethyl group (—SSCH$_3$), for example, 3'-deoxy-dithiomethyl thymidine (see FIG. 3B). In a another embodiment, the modified 5' thiol nucleotides are 5' phosphorothiolate dNTPs.

Other components that are suitable for the kits of the invention include, but are not limited to, an extension buffer (e.g., buffers, salts, magnesium (Mg)), a cleavage buffer, pyrophosphate, one or more supports for isolating extension products, one or more reagents for sample clean-up (e.g., CleanSeq, AmPure) and manufacturer's instructions.

A suitable cleavage buffer comprises a source of one or more metal ions, for example silver, mercury or copper. In a particular embodiment, the cleavage buffer comprises a source of silver ions, such as silver nitrate (AgNO$_3$) or silver acetate. In a further embodiment, the source of silver ions is provided at a concentration in the range of 1-100 mM. Additionally, the cleavage buffer can further comprise a source of magnesium ions (Mg$^{++}$). In a particular embodiment, the source of magnesium ions is magnesium acetate.

EXAMPLE 1

Figure 3A:
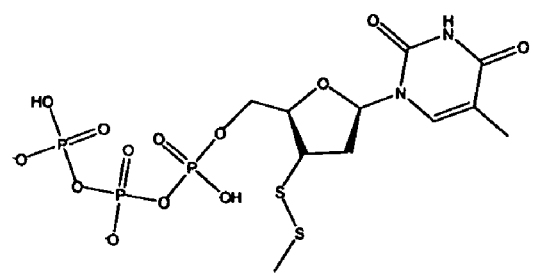
FIG. 3A-FIG. 3E demonstrate the incorporation of 3'-deoxy-dithiomethyl thymidine (dTsTP) into a growing DNA strand by a DNA polymerase.
Figure 3B:
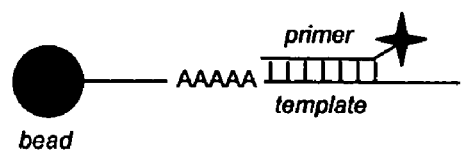
Figure 3C:
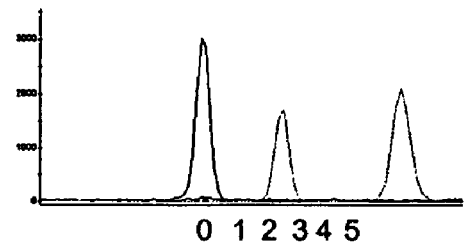

Incorporation of 3' Thiol-Nucleoside Triphosphates into a Growing Strand of DNA by DNA Polymerase Materials and Methods DNA synthesis was performed on a single-stranded DNA template (5'-TTT TTT CTA AGG TAG CGA CTG TCC TAT ACA GAC TGA CAA AAA AAG AGA ATG AGG AAC CCG GGG CAG-3') (SEQ ID NO:1), which was labeled at its 5' end with a dual biotin tag and was attached to a magnetic bead (FIG. 3B). Synthesis was primed using a primer (5'-CTG CCC CGG GTT CCT CAT TCT CT-3') (SEQ ID NO:2), which was complementary to a portion of the DNA template. The primer was labeled with Cy5 at its 5' end. The DNA template contained 5 adenine nucleotides immediately downstream of the primer sequence. Primer extension reactions were performed using 12.5 U exo$^-$ E. coli Polymerase I, Klenow fragment (Epicentre) with 500 μm or 50 μm of 3'-deoxy-dithiomethyl thymidine (dTsTP) at 37° C. for 4.0 min.

Results

Figure 3D:
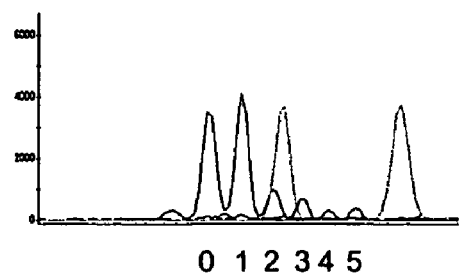
Figure 3E:
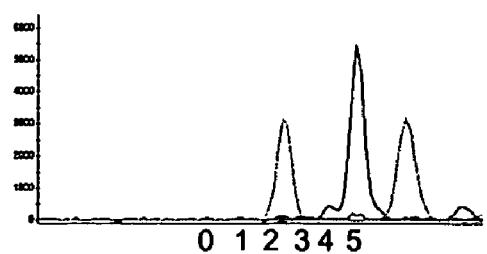

Up to five 3'-deoxy-dithiomethyl thymidine nucleotides were successfully incorporated into the DNA amplification product following completion of the reaction. When present at a low concentration (5.0 μm), DNA products with 0, 1, 2, 3, 4 or 5 modified thymidine residues were recovered (FIG. 3D). The majority of reaction products, however, contained either 0 or 1 modified nucleotide. When present at a higher concentration (1.0 mM), the vast majority of reaction products contained 5 modified thymidine residues (FIG. 3E). Similar results were observed when reactions were conducted using other polymerases, including Sequenase, exo-Taq polymerase and exo-Bst polymerase. These data indicate that modified 3'-deoxy-dithiomethyl thymidine nucleotides can be readily incorporated into a growing DNA strand during synthesis reactions involving DNA polymerase.

EXAMPLE 2

Figure 4A:
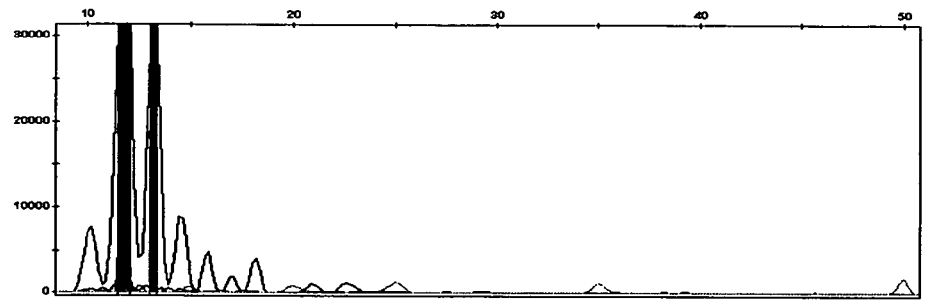
FIG. 4A-FIG. 4E depict incorporation of 3'-deoxy-dithiomethyl thymidine (dTsTP) nucleotides into primer extension products, followed by subsequent cleavage of the nucleotides in the presence of silver.
Figure 4B:
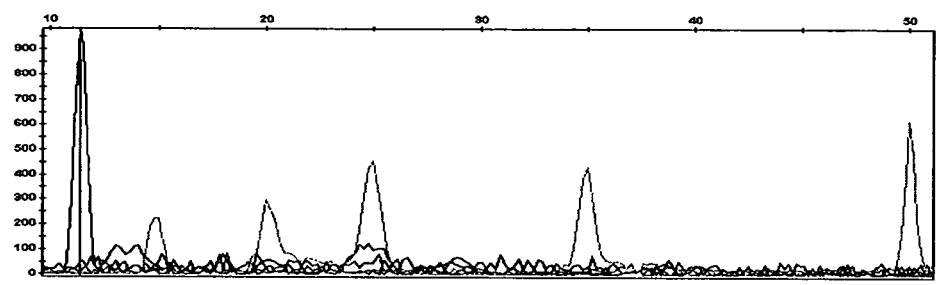
Figure 4C:
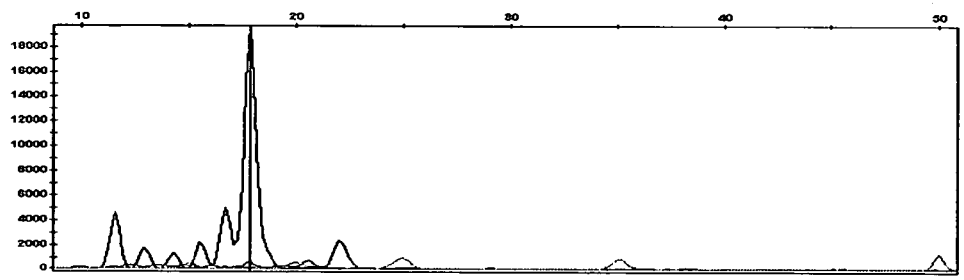
Figure 4D:
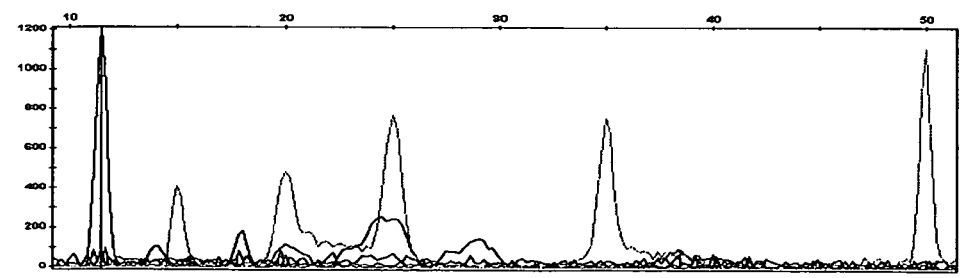
Figure 4E:
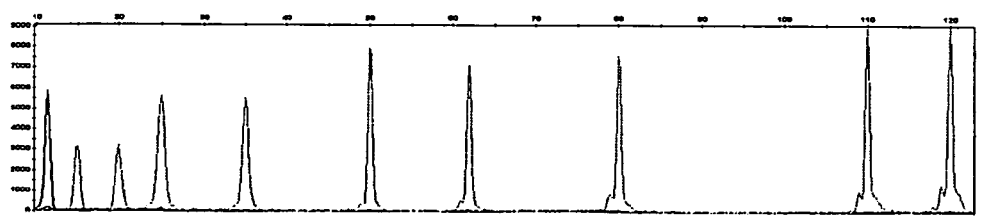

Chemical Cleavage of DNA Containing 3' Thiol Modified Nucleotides in the Presence of Silver Ions Prior to cleavage, modified nucleotides containing five 3' thiol modified thymidine nucleotides on one strand (see Example 1) were washed with 25 mM Magnesium acetate. Cleavage was induced by incubating the products with 10 μl silver nitrate (AgNO$_3$) at a concentration of either 50 μm (FIG. 4B) or 500 μm (FIG. 4D) for 15 min at room temperature. Unbound cleavage fragments were removed by washing in dH$_2$O, and bound reaction products containing the primer were analyzed using a standard gel shift assay. Both concentrations of AgNO$_3$ that were tested resulted in cleavage of the DNA product containing 3' thiol modified thymidine nucleotides (FIG. 4B and FIG. 4D).

EXAMPLE 3

Figure 1B:
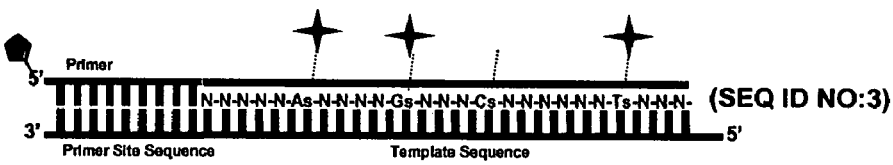
Figure 1C:
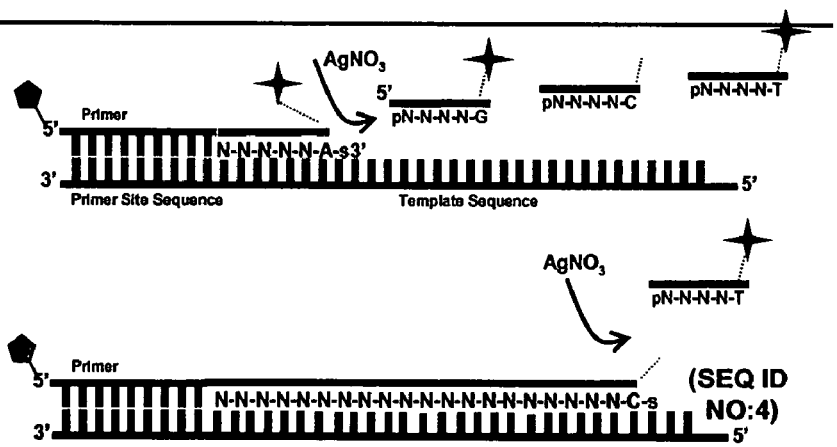
Figure 1D:
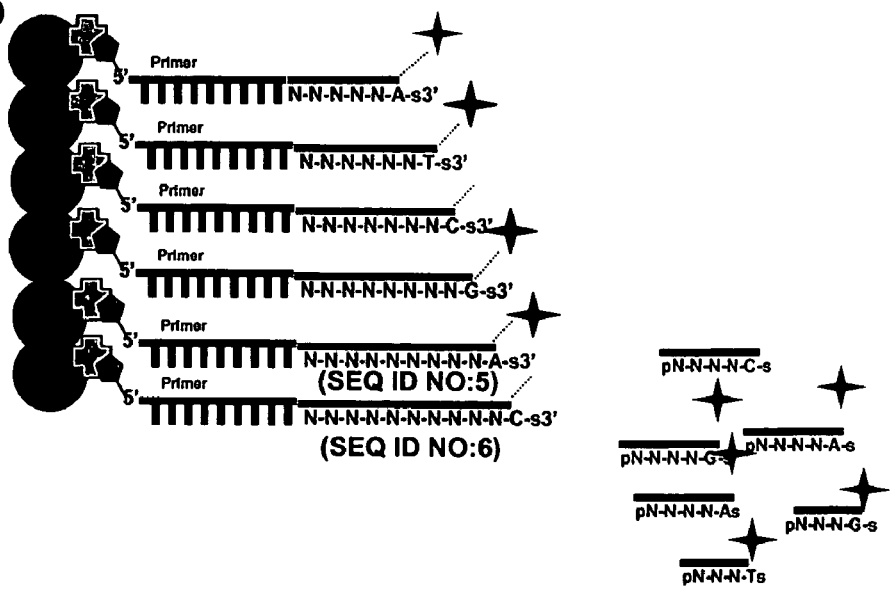
Figure 2A:
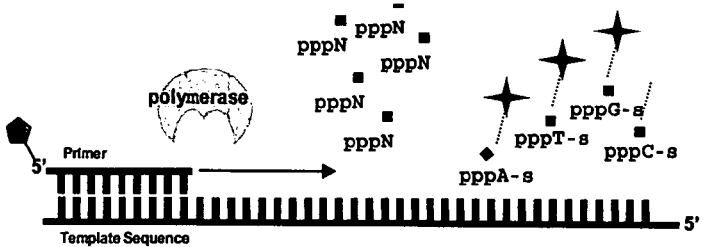
FIG. 2A-FIG. 2C are schematics illustrating the steps involved in producing, cleaving and separating forward and reverse primer extension products, each of which contains a labeled 3' thiol nucleotide at its 3' end.
Figure 2A:
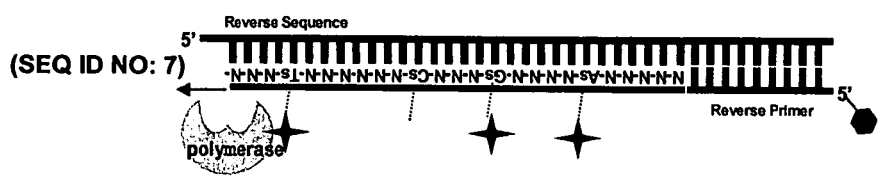
Figure 2B:
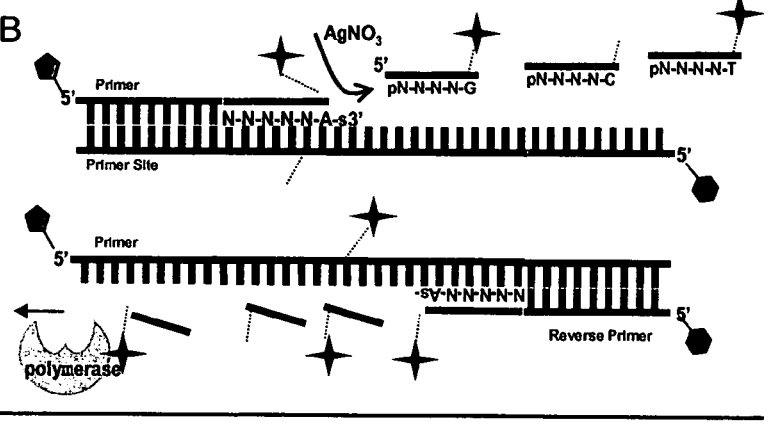
Figure 2C:
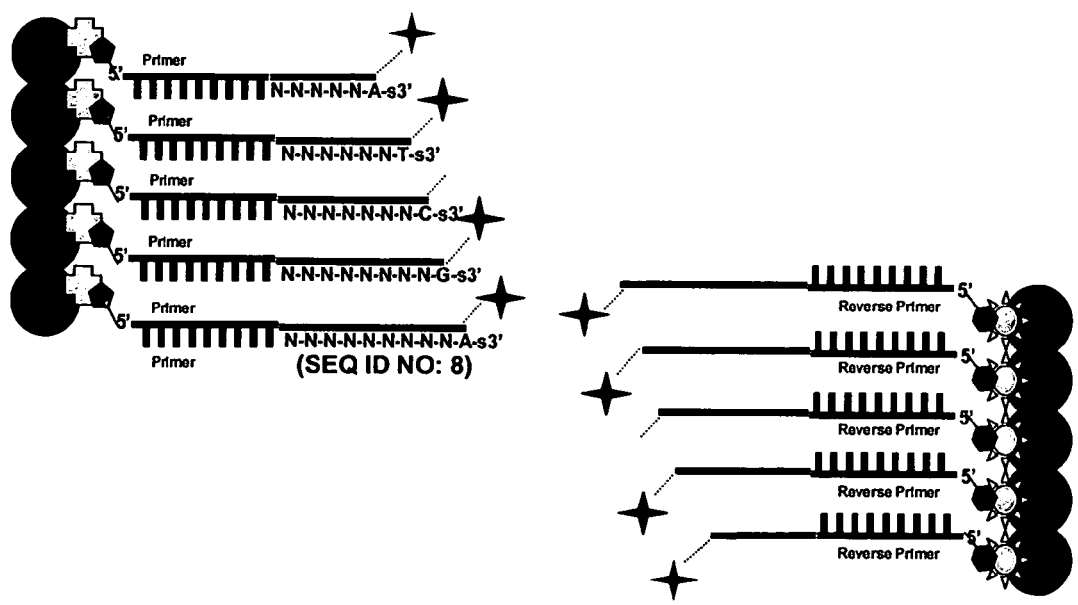
Figure 5:
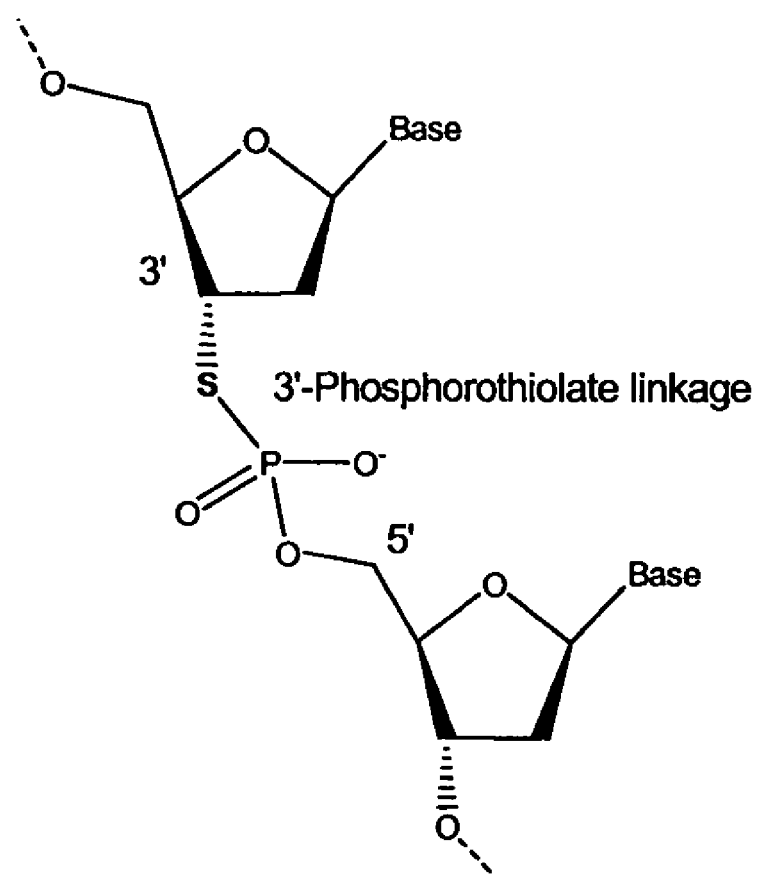
FIG. 5 depicts the chemical structure of a polynucleotide that comprises a 3' phosphorothiolate linkage.

Prophetic Example of DNA Synthesis by Primer Extension with 3' Thiol-Nucleoside Triphosphates (sdNTPs) and Recovery of Chemically-Cleaved Extension Products Primer extension on a DNA template is conducted in the presence of both unmodified nucleoside triphosphates and modified 3'-thiol-nucleoside triphosphates (FIG. 1A). When the modified nucleoside triphosphates are used at a low concentration, they incorporate randomly into the growing DNA strand next to natural dNTPs at a low frequency (FIG. 1B). Incorporation of these modified nucleotides into the DNA introduces one or more 3'-phosphorothiolate linkages (FIG. 5) into the DNA strand. The sulfur-phosphorus bond of a phosphorothiolate linkage are specifically and rapidly cleaved by exposure to silver ions (Ag$^+$). As a consequence, the addition of silver nitrate (AgNO$_3$) to the reaction ensures that each strand containing a phosphorothiolate linkage is cleaved into 2 or more fragments, depending on the number of 3'-thiol nucleotides in the strand (FIG. 1C). If the primers used in the reaction are labeled with an affinity tag, such as biotin, the 5'-most fragments, which contain the primer sequence with the affinity tag, are readily isolated using streptavidin magnetic beads (FIG. 1D). Once captured, the remaining, untagged fragments are washed away. The purified fragments can be resolved by gel electrophoresis, resulting in a fragmentation ladder. If each of the four 3' thiol nucleotide triphosphates are fluorescently-labeled with a distinct fluorophore, the products are analyzed on a standard fluorescence based sequencing instrument to read the sequence of the strand. Furthermore, if polymerase chain reaction (PCR) is conducted using two primers (F FIG. 2A-FIG. 2B), wherein each primer contains a different tag, the 5'-most extension products from both strands are recovered separately and the sequence of both strands could be analyzed (FIG. 2C).

The relevant teachings of all publications cited herein that have not explicitly been incorporated by reference, are incorporated herein by reference in their entirety. While this invention has been particularly shown and described with references to particular embodiments thereof, it will be understood by those skilled in the art that various changes in form and details may be made therein without departing from the scope of the invention encompassed by the appended claim.

What is claimed is:

1. A method for producing a modified polynucleotide sequence comprising:
   a) annealing at least one primer to a template polynucleotide sequence;
   b) extending said primer in the presence one or more nucleoside triphosphates,
   wherein at least one of the nucleoside triphosphates is a modified nucleoside triphosphate comprising a general structure [I]:

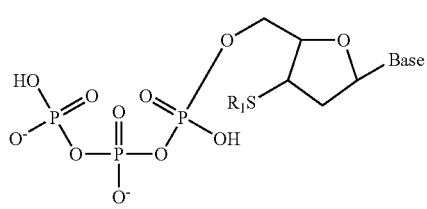

wherein $R_1$ is hydrogen, a substituted or non-substituted: alkyl, akenyl, alkynyl or aryl group, or $R_2$;
   wherein $R_2$ is —SH, or —SR$_3$; and
   wherein $R_3$ is a substituted or non-substituted: alkyl, akenyl, alkynyl or aryl group;
thereby producing a modified polynucleotide sequence comprising at least one modified nucleotide, wherein said modified polynucleotide sequence comprises a general structure [II]:

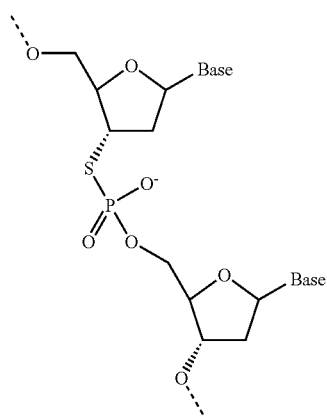

wherein the general structure [II] comprises a 3' phosphorothiolate linkage.

2. The method of claim 1, wherein $R_1$ is hydrogen (—H) or —SCH$_3$.

3. The method of claim 1, wherein the template polynucleotide sequence comprises a sense and an antisense strand and at least one primer is annealed to each strand prior to step (b).

4. The method of claim 1, wherein the primer comprises at least one tag.

5. The method of claim 1, wherein the one or more nucleoside triphosphates comprises a tag.

6. The method of claim 1, wherein the Base in general structure [I] is selected from the group consisting of guanine, adenine, thymine, cytosine, uracil, inosine and 7-deaza-guanine.

7. A method for producing a modified polynucleotide sequence comprising:
   a) annealing at least one primer to a template polynucleotide sequence;
   b) extending said primer in the presence of a mixture of nucleoside triphosphates, wherein at least one of the nucleoside triphosphates is a modified nucleoside triphosphate comprising a general structure [III]:

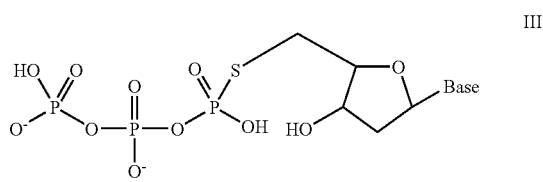

thereby producing a modified polynucleotide sequence comprising at least one modified nucleotide, wherein said modified polynucleotide sequence comprises a general structure [IV]:

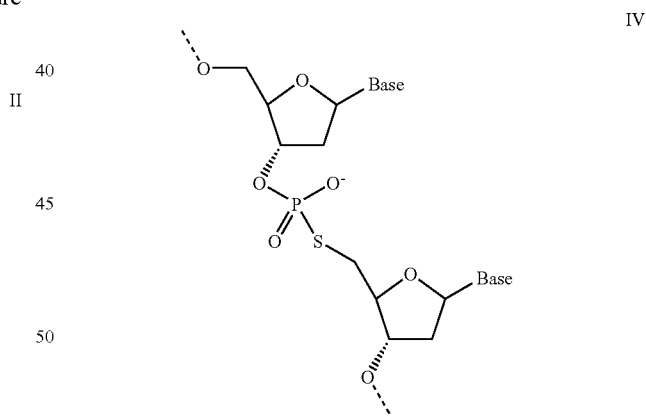

wherein the general structure [IV] comprises a 5' phosphorothiolate linkage.

8. The method of claim 7, wherein the template polynucleotide sequence comprises a sense and an antisense strand and at least one primer is annealed to each strand prior to step (b).

9. The method of claim 7, wherein the at least one primer comprises a first tag.

10. The method of claim 9, wherein the at least one primer further comprises a second tag.

11. The method of claim 7, wherein the Base in general structure [III] is selected from the group consisting of guanine, adenine, thymine, cytosine, uracil, inosine and 7-deaza-guanine.

12. A method for determining a polynucleotide sequence comprising:
   a) annealing a plurality of primers to a plurality of template polynucleotide sequences;
   b) extending the plurality of primers in the presence of one or more nucleoside triphosphates, wherein at least one of the nucleoside triphosphates is a modified nucleoside triphosphate comprising a general structure [I]:

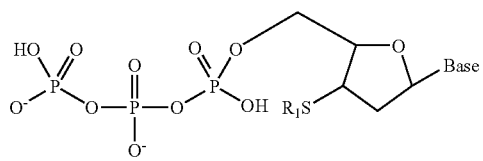

wherein $R_1$ is hydrogen, a substituted or non-substituted: alkyl, akenyl, alkynyl or aryl group, or $R_2$;
   wherein $R_2$ is —SH, or —$SR_3$; and
   wherein $R_3$ is a substituted or non-substituted: alkyl, akenyl, alkynyl or aryl group;
   thereby producing a plurality of extension products that comprise a modified polynucleotide sequence, wherein said modified polynucleotide sequence comprises a general structure [II]:

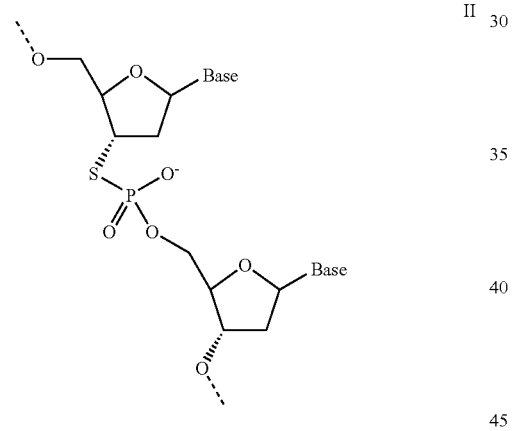

wherein the general structure [II] comprises at least one 3' phosphorothiolate linkage;
   c) cleaving the at least one 3' phosphorothiolate linkage in the extension products under conditions in which a plurality of fragments are produced; and
   d) identifying from among the fragments produced in c), the fragments that comprise the primer; and
   e) identifying the nucleotide at the 3' end of the fragments identified in d), thereby determining a polynucleotide sequence.

13. The method of claim 12, wherein $R_1$ is hydrogen (—H) or —$SCH_3$.

14. The method of claim 12, wherein each template polynucleotide sequence in the plurality of template polynucleotide sequences comprises a sense strand and an antisense strand and wherein at least one primer is annealed to each strand prior to step (b).

15. The method of claim 12, wherein each primer in the plurality of primers comprises comprises a tag.

16. The method of claim 12, wherein the one or more nucleoside triphosphates comprises a tag.

17. A method for determining a polynucleotide sequence comprising:
   a) annealing a plurality of primers to a plurality of template polynucleotide sequences, wherein each primer in the plurality of primers comprises a first tag;
   b) extending the plurality of primers in the presence of one or more nucleoside triphosphates, wherein at least one of the nucleoside triphosphates is a modified nucleoside triphosphate comprising a general structure [III]:

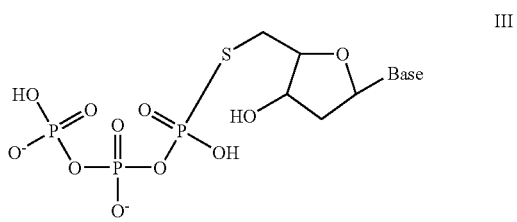

thereby producing a plurality of extension products that comprise a modified polynucleotide sequence having a general structure [IV]:

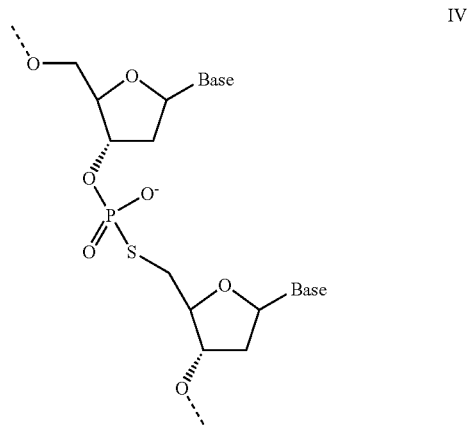

wherein the general structure [IV] comprises at least one 5' phosphorothiolate linkage;
   c) cleaving the at least one 5' phosphorothiolate linkage in the extension products under conditions in which a plurality of fragments are produced; and
   d) identifying from among the fragments produced in c), the fragments that comprise a primer; and
   e) identifying the nucleotide at the 3' end of the fragments identified in d), thereby determining a polynucleotide sequence.

18. The method of claim 17, wherein each template polynucleotide sequence in the plurality of template polynucleotide sequences comprises a sense strand and an antisense strand and wherein at least one primer is annealed to each strand prior to step (b).

19. The method of claim 17, wherein each primer in the plurality of primers further comprises a second tag.

* * * * *

```
                              SEQUENCE LISTING

<160> NUMBER OF SEQ ID NOS: 8

<210> SEQ ID NO 1
<211> LENGTH: 66
<212> TYPE: DNA
<213> ORGANISM: Artificial Sequence
<220> FEATURE:
<223> OTHER INFORMATION: template sequence

<400> SEQUENCE: 1 tttttctaa ggtagcgact gtcctataca gactgacaaa aaaagagaat gaggaacccg      60
gggcag                                                                66

<210> SEQ ID NO 2
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 2
ctgccccggg ttcctcattc tct                                             23

<210> SEQ ID NO 3
<211> LENGTH: 25
<212> TYPE: DNA
<213> ORGANISM: Artificial Sequence
<220> FEATURE:
<223> OTHER INFORMATION: hypothetical primer extension product
<220> FEATURE:
<221> NAME/KEY: modified_base
<222> LOCATION: 6, 11, 15, 22
<223> OTHER INFORMATION: 3' thiol modification
<220> FEATURE:
<221> NAME/KEY: misc_feature
<222> LOCATION: 1, 2, 3, 4, 5, 7, 8, 9, 10, 12, 13, 14, 16, 17, 18, 19,
      20, 21, 23, 24, 25
<223> OTHER INFORMATION: n = A,T,C or G

<400> SEQUENCE: 3
nnnnnannnn gnnncnnnnn ntnnn                                           25

<210> SEQ ID NO 4
<211> LENGTH: 21
<212> TYPE: DNA
<213> ORGANISM: Artificial Sequence
<220> FEATURE:
<223> OTHER INFORMATION: hypothetical primer extension product
<220> FEATURE:
<221> NAME/KEY: modified_base
<222> LOCATION: 21
<223> OTHER INFORMATION: 3' thiol modification
<220> FEATURE:
<221> NAME/KEY: misc_feature
<222> LOCATION: 1, 2, 3, 4, 5, 6, 7, 8, 9, 10, 11, 12, 13, 14, 15, 16,
      17, 18, 19, 20
<223> OTHER INFORMATION: n = A,T,C or G

<400> SEQUENCE: 4
nnnnnnnnnn nnnnnnnnnn c                                               21
```

<210> SEQ ID NO 5
<211> LENGTH: 10
<212> TYPE: DNA
<213> ORGANISM: Artificial Sequence
<220> FEATURE:
<223> OTHER INFORMATION: hypothetical primer extension product
<220> FEATURE:
<221> NAME/KEY: modified_base
<222> LOCATION: 10
<223> OTHER INFORMATION: 3' thiol modification
<220> FEATURE:
<221> NAME/KEY: misc_feature
<222> LOCATION: 1, 2, 3, 4, 5, 6, 7, 8, 9
<223> OTHER INFORMATION: n = A,T,C or G

<400> SEQUENCE: 5 nnnnnnnnna                                                              10

<210> SEQ ID NO 6
<211> LENGTH: 11
<212> TYPE: DNA
<213> ORGANISM: Artificial Sequence
<220> FEATURE:
<223> OTHER INFORMATION: hypothetical primer extension product
<220> FEATURE:
<221> NAME/KEY: modified_base
<222> LOCATION: 11
<223> OTHER INFORMATION: 3' thiol modification
<220> FEATURE:
<221> NAME/KEY: misc_feature
<222> LOCATION: 1, 2, 3, 4, 5, 6, 7, 8, 9, 10
<223> OTHER INFORMATION: n = A,T,C or G

<400> SEQUENCE: 6
nnnnnnnnnn c                                                            11

<210> SEQ ID NO 7
<211> LENGTH: 25
<212> TYPE: DNA
<213> ORGANISM: Artificial Sequence
<220> FEATURE:
<223> OTHER INFORMATION: hypothetical primer extension product
<220> FEATURE:
<221> NAME/KEY: modified_base
<222> LOCATION: 6, 11, 15, 22
<223> OTHER INFORMATION: 3' thiol modification
<220> FEATURE:
<221> NAME/KEY: misc_feature
<222> LOCATION: 1, 2, 3, 4, 5, 7, 8, 9, 10, 12, 13, 14, 16, 17, 18, 19,
      20, 21, 23, 24, 25
<223> OTHER INFORMATION: n = A,T,C or G

<400> SEQUENCE: 7
nnnnnannnn gnnncnnnnn ntnnn                                             25

<210> SEQ ID NO 8
<211> LENGTH: 10
<212> TYPE: DNA
<213> ORGANISM: Artificial Sequence
<220> FEATURE:
<223> OTHER INFORMATION: hypothetical primer extension product
<220> FEATURE:
<221> NAME/KEY: modified_base
<222> LOCATION: 10
<223> OTHER INFORMATION: 3' thiol modification
<220> FEATURE:
<221> NAME/KEY: misc_feature
<222> LOCATION: 1, 2, 3, 4, 5, 6, 7, 8, 9
<223> OTHER INFORMATION: n = A,T,C or G

```
<400> SEQUENCE: 8 nnnnnnnnna                                                              10
```